(12) United States Patent
Marka et al.

(10) Patent No.: US 10,007,408 B2
(45) Date of Patent: Jun. 26, 2018

(54) MEDICAL CONTROL SYSTEMS

(71) Applicant: Trumpf Medizin Systeme GmbH + Co. KG, Saalfeld (DE)

(72) Inventors: Rudolf Marka, Ismaning (DE); Serhan Oezhan, Munich (DE); Tim Schwebel, Inning (DE); Gel Han, Munich (DE)

(73) Assignee: TRUMPF MEDIZIN SYSTEME GMBH + CO. KG, Saalfeld (DE)

( * ) Notice: Subject to any disclaimer, the term of this patent is extended or adjusted under 35 U.S.C. 154(b) by 432 days.

(21) Appl. No.: 14/710,684

(22) Filed: May 13, 2015

(65) Prior Publication Data

US 2015/0317068 A1 Nov. 5, 2015

Related U.S. Application Data

(63) Continuation of application No. PCT/EP2013/073750, filed on Nov. 13, 2013.

(30) Foreign Application Priority Data

Nov. 13, 2012 (DE) ........................ 10 2012 220 672

(51) Int. Cl.
*G06F 3/0484* (2013.01)
*G06F 3/0488* (2013.01)
(Continued)

(52) U.S. Cl.
CPC .......... *G06F 3/04842* (2013.01); *A61B 34/25* (2016.02); *A61B 90/30* (2016.02);
(Continued)

(58) Field of Classification Search
CPC ............... G06F 19/3406; G06F 19/321; G06F 19/3456; G06F 19/322; G06F 19/327;
(Continued)

(56) References Cited

U.S. PATENT DOCUMENTS 5,300,926 A 4/1994 Stoeckl
8,244,824 B2 * 8/2012 Garibaldi ............ G06F 19/3406
600/300
(Continued)

FOREIGN PATENT DOCUMENTS

DE 102008043531 A1 5/2010
EP 1010404 A2 6/2000
(Continued)

OTHER PUBLICATIONS

Switchpoint Infinity (TM) Control System Operations and Maintenance Manual, Jan. 1, 2004, XP055128973, retrieved from the internet: http://aamedicalstore.com/media/manuals/Stryker Switchpoint Infinity Manual.pdf, 61 pages.
(Continued)

*Primary Examiner* — Tadesse Hailu
(74) *Attorney, Agent, or Firm* — Barnes & Thornburg LLP (57) ABSTRACT

A medical control system includes an operator device having a touchscreen, a control device, and several medical apparatuses, wherein the medical apparatuses and the operator device are coupled to the control device by respective data connections. The operator device is adapted to display several schematic illustrations respectively corresponding to the medical apparatuses in a first display, and the operator device is adapted, by touching a first schematic illustration of a first medical apparatus, to illustrate the first medical apparatus along with first specific operation functions of the first medical apparatus in a second display, wherein substantially similar specific operation functions of the medical apparatuses are illustrated by substantially similar symbols.

28 Claims, 9 Drawing Sheets

(51) Int. Cl.
    *A61G 13/02* (2006.01)
    *H05B 33/08* (2006.01)
    *A61B 90/30* (2016.01)
    *A61B 34/00* (2016.01)
    *G16H 40/63* (2018.01)
    *A61B 17/00* (2006.01)
    *A61B 90/00* (2016.01)

(52) U.S. Cl.
CPC ........... *A61G 13/02* (2013.01); *G06F 3/0488* (2013.01); *G16H 40/63* (2018.01); *H05B 33/0803* (2013.01); *A61B 2017/00199* (2013.01); *A61B 2017/00221* (2013.01); *A61B 2017/00225* (2013.01); *A61B 2034/258* (2016.02); *A61B 2090/372* (2016.02); *A61G 2203/16* (2013.01); *A61G 2203/20* (2013.01)

(58) Field of Classification Search
CPC ............... G06F 19/3412; G06F 19/345; G06F 3/04845; G06F 3/04842; G06F 3/0488; A61B 34/25; A61B 90/30; G16H 40/63; H05B 33/0803
See application file for complete search history.

(56) References Cited

U.S. PATENT DOCUMENTS

| | | | |
|---|---|---|---|
| 2002/0111701 A1 | 8/2002 | Borders | |
| 2003/0195644 A1* | 10/2003 | Borders | A47C 31/008 700/90 |
| 2004/0052076 A1 | 3/2004 | Mueller et al. | |
| 2005/0125897 A1 | 6/2005 | Wyslucha et al. | |
| 2006/0101581 A1* | 5/2006 | Blanchard | A61G 7/00 5/713 |
| 2007/0138966 A1* | 6/2007 | Marka | F21V 23/04 315/76 |
| 2008/0235872 A1* | 10/2008 | Newkirk | A61G 7/018 5/600 |
| 2009/0112630 A1* | 4/2009 | Collins, Jr. | G06F 19/327 705/3 |
| 2010/0138524 A1* | 6/2010 | Sobie | A61B 5/0002 709/222 |

FOREIGN PATENT DOCUMENTS

| | | |
|---|---|---|
| EP | 1181897 A2 | 2/2002 |
| EP | 1677224 A2 | 7/2006 |
| EP | 1394717 B1 | 11/2011 |

OTHER PUBLICATIONS

"Tegris Redefining or Integration", Oct. 1, 2012, XP055129429, Rastatt, Germany, retrieved from the Internet: http://www.maquet.com/content/SurgicalWorkplaces/Documents, 16 pages.

Notification of Transmittal of Translation of the International Preliminary Report on Patentability and Written Opinion for corresponding PCT Application No. PCT/EP2013/073750, 10 pages.

Chinese Office Action issued in connection with Chinese Application No. 201380064501.X, dated Sep. 29, 2016, 9 pages (Chinese language).

* cited by examiner

MEDICAL CONTROL SYSTEMS

CROSS-REFERENCE TO RELATED APPLICATIONS

This application is a continuation of and claims priority under 35 U.S.C. § 120 to PCT Application No. PCT/EP2013/073750 filed on Nov. 13, 2013, which claimed priority to German Application No. DE 10 2012 220 672.8, filed on Nov. 13, 2012. The contents of both of these priority applications are hereby incorporated by reference in their entirety.

TECHNICAL FIELD

The present disclosure relates to medical control systems, particularly those in connection with an operator device that has a touchscreen.

BACKGROUND

Medical control systems are capable of controlling several different medical apparatuses. For example, images of user interfaces of different medical apparatuses can be depicted on a touchscreen. Operating the different medical apparatuses can be challenging when the user interfaces of the different medical apparatuses are not operated in a uniform manner.

SUMMARY

Implementations of the present disclosure provide a medical control system enabling an intuitive operation of different medical apparatuses by a respective user interface having a uniform appearance and a uniform operating concept.

By such a medical control system, substantially similar specific operation functions of the different medical apparatuses are depicted by substantially similar symbols, whereby a simple and intuitive operation of the medical apparatuses is possible.

In some embodiments of the medical control system, the medical apparatuses are depicted such that the arrangement of the depicted positions of the medical apparatuses corresponds to the arrangement from the view from the operator device, whereby a simple and intuitive operation of the medical apparatuses is possible.

Other aspects, features, and advantages will be apparent from the description, the claims, and the drawings.

DETAILED DESCRIPTION

Figure 1:
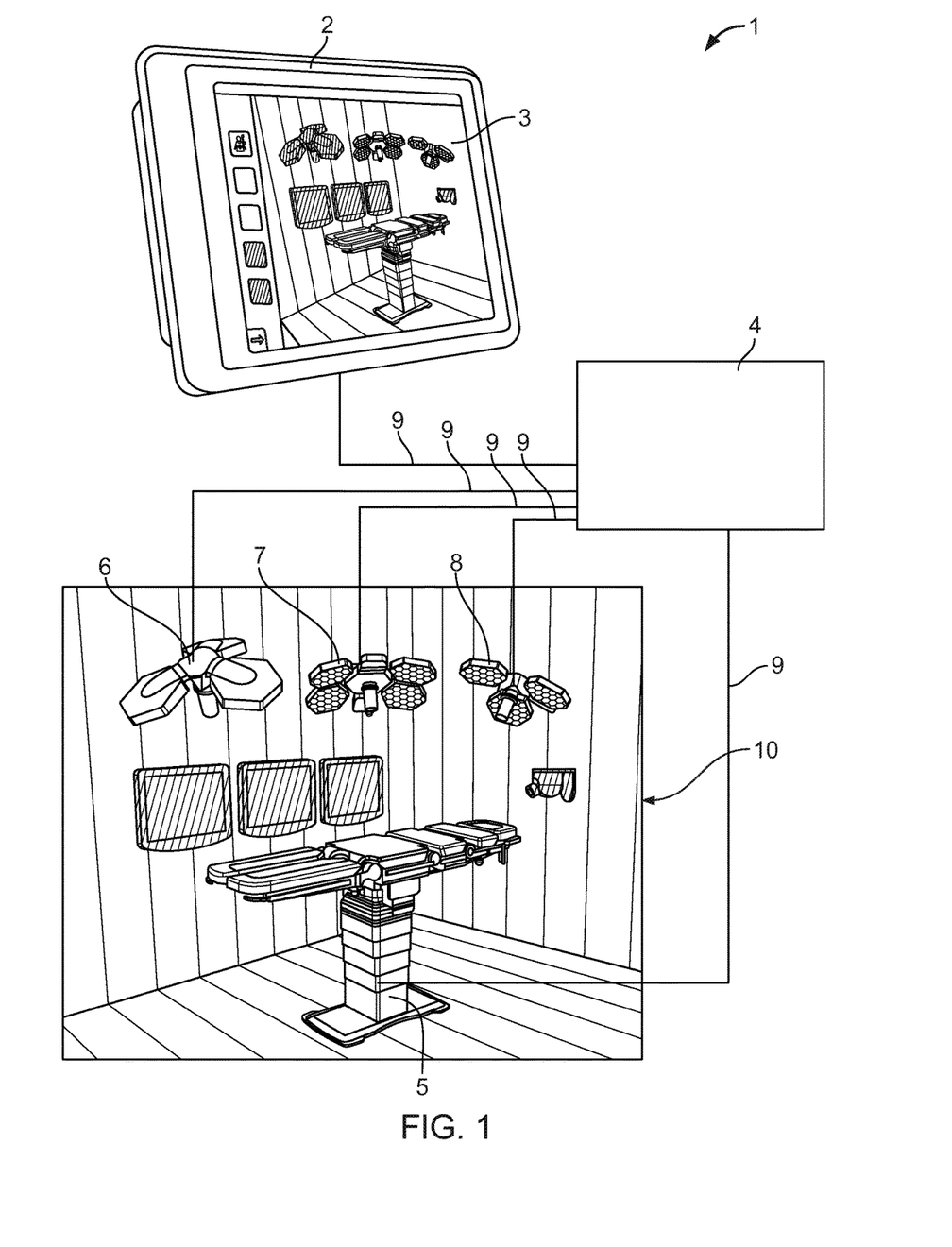
FIG. 1 shows a medical control system.

FIG. 1 shows a medical control system 1. The medical control system 1 includes an operator device 2 in the form of a tablet computer having a touchscreen 3, a control device 4, and several medical apparatuses in the form of a surgical table 5 and surgical lamps 6, 7, 8 in an operating room 10. The medical apparatuses 5, 6, 7, 8 are connected to the control device 4 by data connections 9. The control device 4 can be a portion of the operator device 2, itself, or can be a portion of a separate device.

The equipment of the medical control system 1 in this embodiment is exemplary. In alternative embodiments, another number, other types, and other arrangements of the medical apparatuses 5, 6, 7, 8 are possible. The medical control system 1 is also not limited to an operating room 10, but can alternatively be used in other procedure rooms or in an intensive care unit.

The operator device 2 serves for creating a steady (e.g., immobile or fixed) operation unit or, optionally, a mobile operation unit additionally or alternatively to the operation equipment provided at the medical apparatuses 5, 6, 7, 8. For a steady design, the operator device 2 is fixed to a wall or accommodated in a docking station that is fixed to the wall or, for example, to a medical supply unit. In the case of a docking station, it is possible to establish a data connection 9 via the docking station and to supply the operator device 2 with electrical energy. There is also the option to remove the operator device 2 from the docking station and to use the operator device 2 in a mobile manner. The data connection 9 takes place via a cable or, alternatively, via a wireless connection (e.g., a radio or infrared signal). The operator device 2 may either be operated in the unsterile area or, if used with an appropriate sterilizable equipment, in the sterile area of the operating room 10.

The touchscreen 3 shown in FIG. 1 shows an illustration of the operating room 10 and a schematic illustration of the medical apparatuses 5, 6, 7, 8. The medical apparatuses 5, 6, 7, 8 that will not be operated by the operator device 2 (in this case, the surgical lamp 6) are shown as dimmed on the touchscreen 3.

The equipment of the actual operating room 10 is recognized by a localization service in a superior system, and all the medical apparatuses 5, 6, 7, 8 located in the room are displayed on a start screen on the touchscreen 3. Therefore, the user sees the medical apparatuses 5, 6, 7, 8 located in the operating room 10. Alternatively, it is also possible to display or to operate the medical apparatuses 5, 6, 7, 8 in a user-specific or use-specific manner (e.g., for specific surgeries). The recognized apparatuses 5, 6, 7, 8 can also alternatively be displayed in an arrangement either according to a preconfigured user screen, in an arrangement actually recognized by the localization service (as discussed below), or in an arrangement stored in the medical control system 1.

Furthermore, a dynamic display of the medical apparatuses 5, 6, 7, 8 is possible. Upon a change of the position of the medical apparatuses 5, 6, 7, 8, the actual positions are displayed on the touchscreen 3 so that a potential risk of collision among the medical apparatuses 5, 6, 7, 8 can be recognized.

In an alternative embodiment, the illustration of the operating room 10 is provided such that the medical apparatuses 5, 6, 7, 8 are arranged at predefined positions in the operating room 10. The medical apparatuses 5, 6, 7, 8 are displayed at the predefined positions. The illustration of the operating room 10 is three-dimensional. However, in some implementations, the illustration of the operating room 10 can alternatively be two-dimensional. In a further alternative embodiment, the illustration is dynamic so that the illustration of the medical apparatuses 5, 6, 7, 8 is modified to correspond to a view towards the medical apparatuses 5, 6, 7, 8 from the operator device 2.

Figure 2:
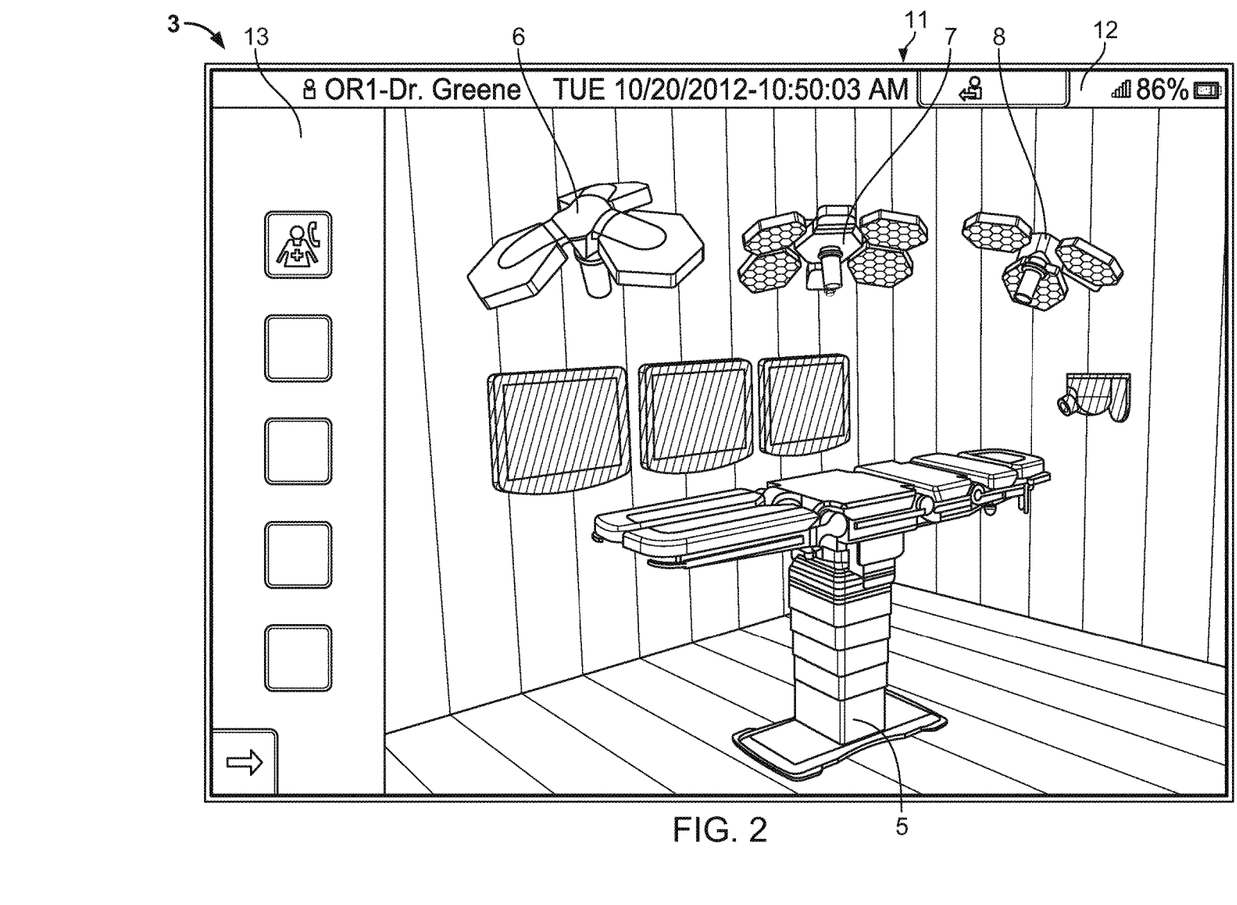
FIG. 2 shows a first display of a touchscreen of an operator device of the medical control system of FIG. 1 that illustrates several medical apparatuses of the medical control system of FIG. 1.

In FIG. 2, the start screen on the touchscreen 3 is shown as a first display 11. The first display 11 shows the medical apparatuses 5, 6, 7, 8 in the form of the surgical table 5 and the surgical lamps 6, 7, 8 being connected to the control device 4 and being operable by the operator device 2. Further apparatuses, such as monitors and a camera, are shown as dimmed, such that they can be recognized as not being operable by the operator device 2. Furthermore, in some cases, medical apparatuses 5, 6, 7, 8 recognized by the localization service and displayed may not be operable by the medical control system 1 (e.g., due to an incompatibility). In such cases, these medical apparatuses 5, 6, 7, 8 are also shown as dimmed.

Furthermore, a status line 12 is depicted, and a favorite bar 13 can be displayed on the first display 11 and also on further displays. In the status line 12, the number of the operating room 10 ("OR1"), the actual user of the medical control system 1 ("Dr. Greene"), the actual date, and the actual time are displayed. Also, a "log-out button" for logging out from the medical control system 1 is provided, and a display of a state of charge of an accumulator battery of the operator device 2 is provided. In the favorite bar 13, a button for "call floater" is shown in this example. Further favorite buttons can be displayed and activated in a user-specific or use-specific manner.

In use, by touching the illustration of one of the medical apparatuses 5, 6, 7, 8 on the first display 11 of the touchscreen 3, a further display is activated in which the specific operation functions of the touched medical apparatuses 5, 6, 7, 8 are displayed. In this example, a schematic illustration of the surgical table 5 is touched on the touchscreen 3.

Figure 3:
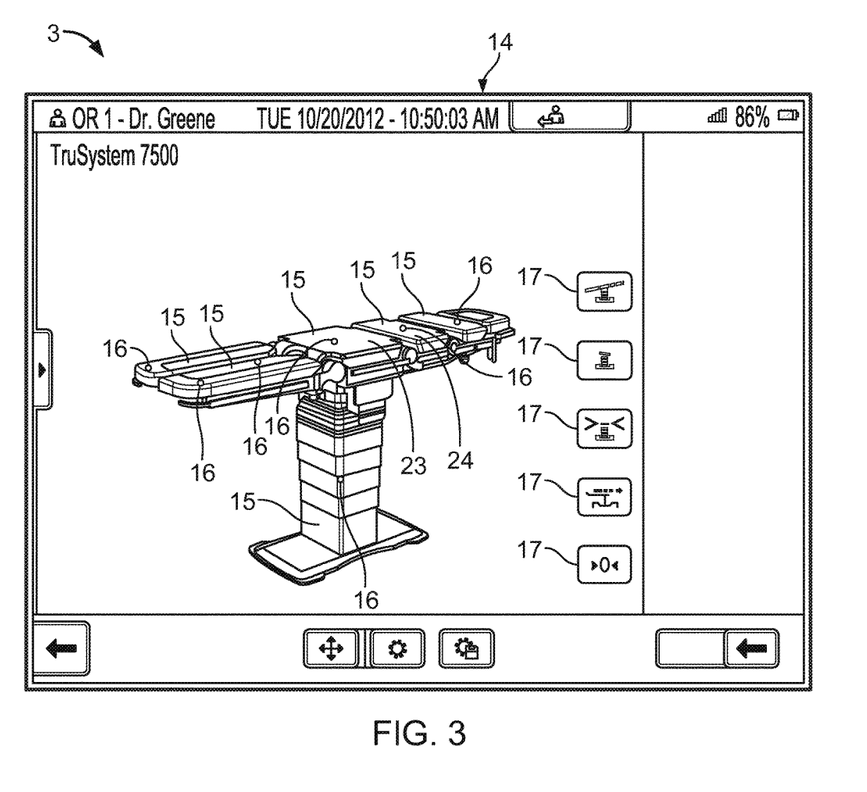
FIG. 3 shows a second display of the touchscreen of FIG. 2 with an illustration of a surgical table as one of the several medical apparatuses of FIG. 2 and of symbols for specific operation functions.

In FIG. 3, the further display is optionally illustrated as a second display 14 on the touchscreen 3. In the second display 14, driven components 15 of the surgical table 5 are illustrated. The driven components 15 or groups of the driven components 15 are marked by small circles 16 in order to control the driven components 15 by specific operation functions. Furthermore, symbols 17 for further specific operation functions (e.g., for a movement of groups of the driven components 15 which, due to their complexity, can no longer be selected by controlling individual driven components 15 in predefined directions) are displayed. For example, the approach of a Trendelenburg position is indicated by the topmost symbol 17, and the approach of a zero position is indicated by the lowest symbol 17 so that substantially similar operation functions are illustrated by substantially similar symbols.

In use, by touching the circle on the illustration of one of the driven components 15, a further display is activated on which a possible direction of movement and defaults for a possible speed of movements are displayed, or the illustration is extended in a function-specific manner. In this example, the circle on the surgical table top segment 23 ("lower back") is touched.

Figure 4:
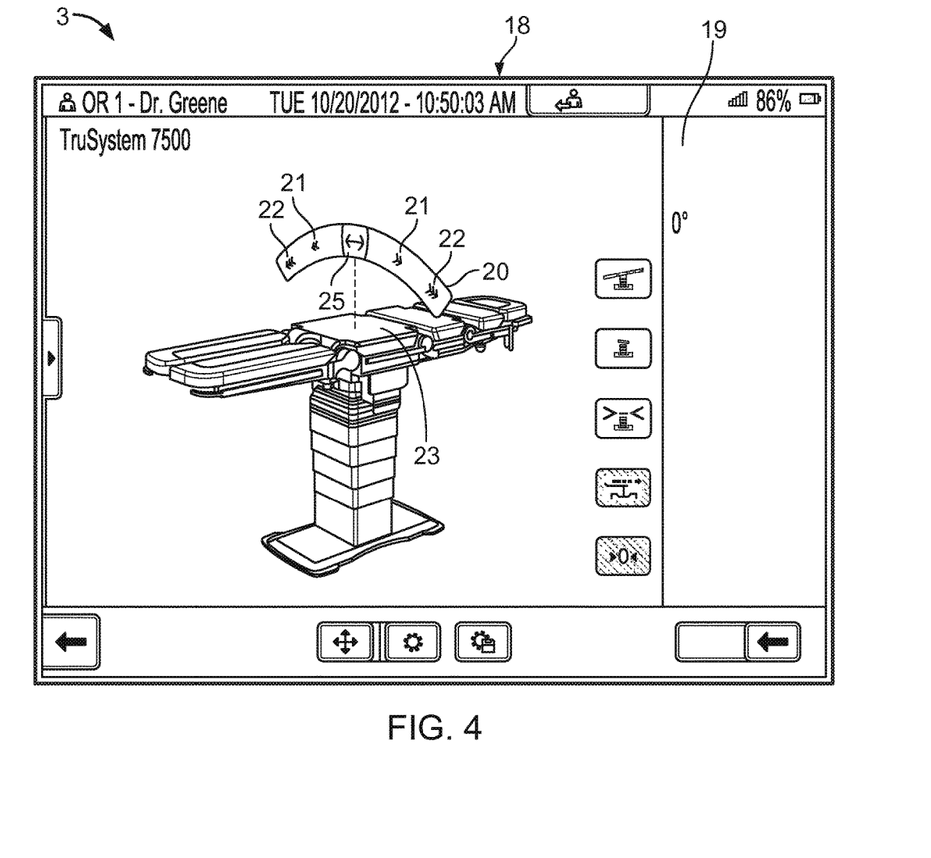
FIG. 4 shows a third display of the touchscreen of FIG. 2 with an illustration of the one medical apparatus of FIG. 2 and of a pointer for a direction of movement and a possible speed of movements.

In FIG. 4, a further display is shown as a third display 18 on the touchscreen 3. Above the surgical table top segment 23, a circular arc segment 20 showing the direction of movement of the specific operation function of the surgical table 5 (in this example, a tilt function) is displayed. In the course of circular arc segment 20 starting from its center in both directions, a double arrow 21 and a triple arrow 22 are shown. The arrows 21, 22 depict a possible speed of movements of the specific operation function. In an information column 19, a tilt angle (in this example, 0 degrees) is optionally illustrated as information of an actual position in the possible direction of movement.

Figure 5:
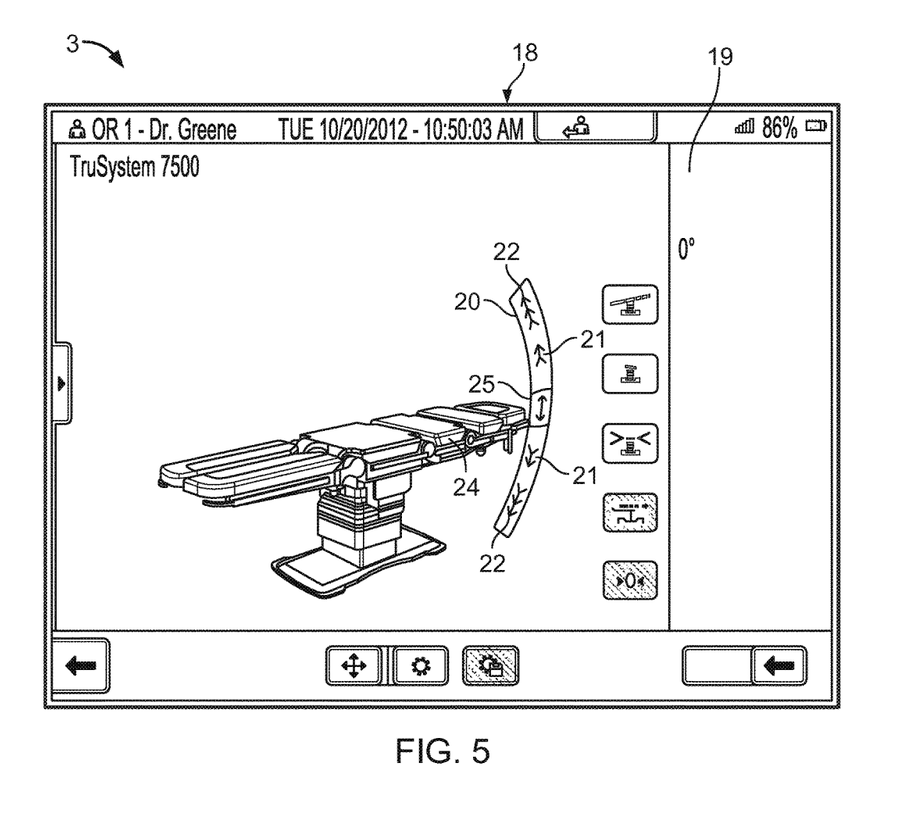
FIG. 5 shows the third display of FIG. 4 with the illustration of the medical apparatus of FIG. 2 and of a pointer for a direction of movement and a possible speed of movements different from the direction and speed of movements shown in FIG. 4.

In FIG. 5, another implementation of a third display 18 illustrated on the touchscreen 3 is shown. The difference between the third display 18 of FIG. 5 and the display shown in FIG. 4 is that, by a foregoing touching of the circle 16 on the surgical table top segment 24 ("back") on the second display 14 (shown in FIG. 3), the specific operation function for the movement of the surgical table top segment 24 ("back") is shown. Here, a pivoting of the upper three surgical table top segments is depicted as the possible direction of movement by the appropriate circle segment 20 and as the possible speed by the double arrows 21 and triple arrows 22. Therefore, the operation functions in FIG. 4 and FIG. 5 are displayed by identical symbols so that substantially similar operation functions are illustrated by substantially similar symbols.

In use, the operation functions are activated by touching a double arrow pointer 25 and by moving along the circular arc segment 20 during touching. The speed of the operation function depends on the extent of the moving along the circular arc 22. Further movement along the circular segment 22 increases the speed at which the operation function is executed. In the information column 19, the tilting angle (e.g., the actual position in the possible direction of movement) of the surgical table top 24 is displayed.

Figure 6:
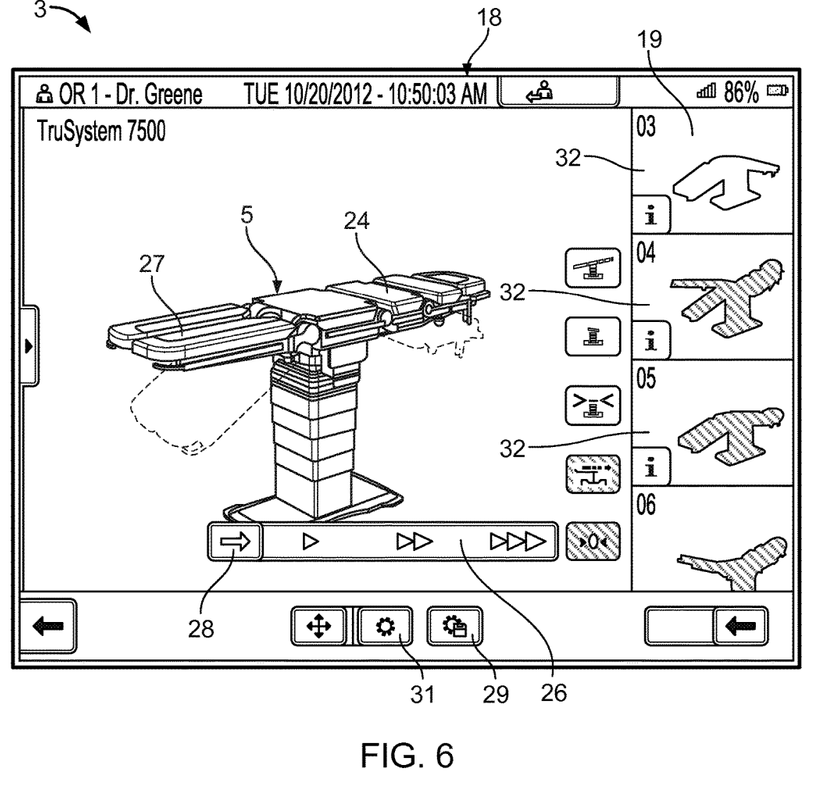
FIG. 6 shows the third display of FIG. 4 with an illustration of the one medical apparatus of FIG. 2 and of end positions of driven components of the medical apparatus and a possible speed of movements of the driven components into the end positions.

In FIG. 6, the third display 18 on the touchscreen 3 optionally shows the surgical table 5, wherein end positions of the driven components 15 and a possible speed of movements are illustrated by the double arrow 21 and the triple arrow 22 in a bar 26. By touching a preset key 31, several preset symbols 32, by which the end positions for the driven components 15 are depicted on the touchscreen 3 as different predefined positions and can be approached, are optionally depicted in the information column 19. The driven components 15 are, in this example, leg plates 27 and the surgical table top segment 24.

In use, the approach of the predefined positions is enabled by touching one of the preset symbols 32. A displacement of the driven components 15 is then activated by touching an arrow pointer 28 and movement of the arrow pointer 28 along the bar 26 during touching. The speed of the operation function depends of the extent of movement along the bar 26. Further movement along the bar 26 increases the speed at which the operation function is executed.

The operation function of a default speed of movements for the approach of predefined positions is therefore substantially equal to that of the default speed of movements of a table top segment shown in FIG. 4 and FIG. 5. Accordingly, substantially identical operation functions are illustrated by substantially identical symbols. Further, a saving symbol 29 is optionally shown in the third display 18.

In use, the medical control device 1 stores the respective actual positions of the driven components 15 when the saving symbol 29 is touched. Accordingly, a further preset symbol 32 is optionally created in the information column 19. The created preset symbol 32 corresponds to an image of the stored position (e.g., the end position of the surgical table 5 corresponding to the preset selection). In addition to the approach of an end position of the surgical table 5, a preset symbol 32 can also be used to move a requested group of components 15 in a predefined relationship with respect to each other.

Figure 7:
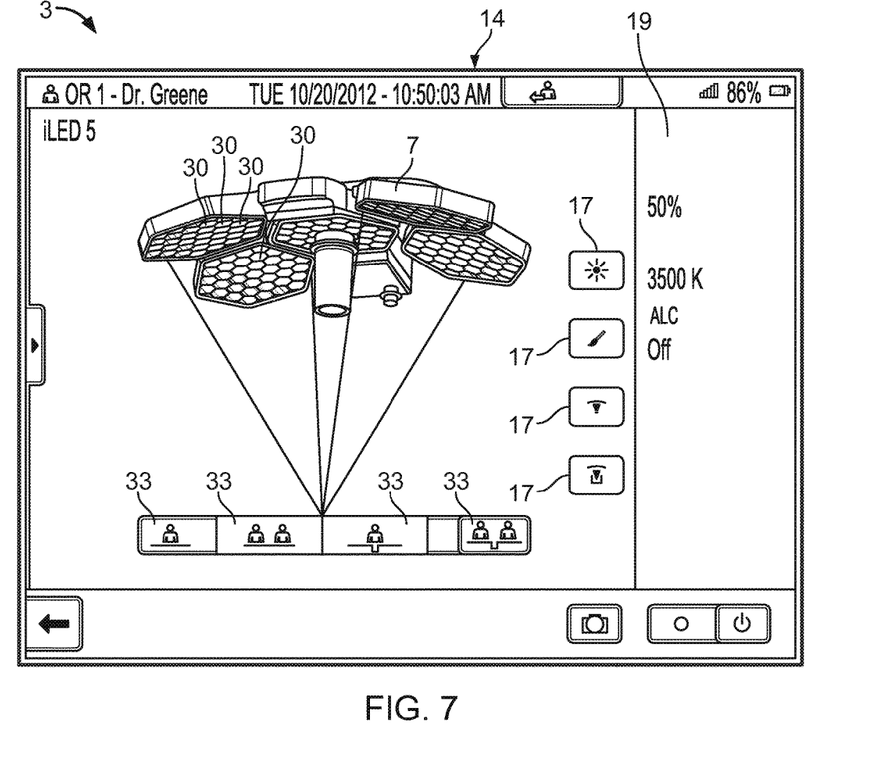
FIG. 7 shows the second display of FIG. 2 with an illustration of a surgical lamp as one of the several medical apparatuses of FIG. 2 and of symbols for specific operation functions.

In FIG. 7, the second display 14 of the touchscreen 3 with an illustration of the surgical lamp 7 as one of the several medical apparatuses 5, 6, 7, 8 and with an illustration of specific operation functions is shown. The surgical lamp 7 includes lighting components 30 creating a light field on a surgical site. In alternative embodiments, the lighting components 30 are provided for general illumination of the operating room 10 or general illumination of another room.

Furthermore, the symbols 17 for the specific operation functions of the surgical lamp 7 are optionally illustrated. In this example, the specific operation functions corresponding to the symbols, from top to bottom, are a brightness setting, a color temperature setting, a setting of a light field size, and a selection of operated lighting components 30. By touching the symbols 17 for the specific operation functions, symbols 33 for adjustable parameters of these operation functions are shown.

In FIG. 7, the specific function "selection of operated lighting components" is selected. Accordingly, the symbols 33 for the adjustable parameters are displayed. In this example, the selection of the operated lighting components is dependent on parameters including whether one or several surgeons operate and whether the surgical wound is flat or deep according to the symbols 33. In the information column 19, the actual adjustments of parameters (i.e., 50% of the brightness, a color temperature of 3500 K, and an off state of the autofocus function (ALC)) are shown. In use, one of the symbols 17 for the specific operation functions on the touch screen 3 are touched and, accordingly, the symbols 33 for adjustable parameters are displayed. By touching one of the symbols 33 for adjustable parameters, the corresponding lighting components 30 of the surgical lamp 7 are controlled in order to execute the selected specific operation function.

By the substantially similar operation sequence and the substantially similar illustration of the type of the operation elements of the medical control system 1, the operation concept for all medical apparatuses 5, 6, 7, 8 is uniform so that the operation can be simplified and can be safely performed. The safe and simplified operation is supported in this way that an illustration of the arrangement of the medical apparatuses 5, 6, 7, 8 on the operator device 2 corresponds to the arrangement of the medical apparatuses 5, 6, 7, 8 in the operating room 10 from a view of the operator device 2. Therefore, a simple and intuitive operation of the medical apparatuses 5, 6, 7, 8 is possible.

Figure 8:
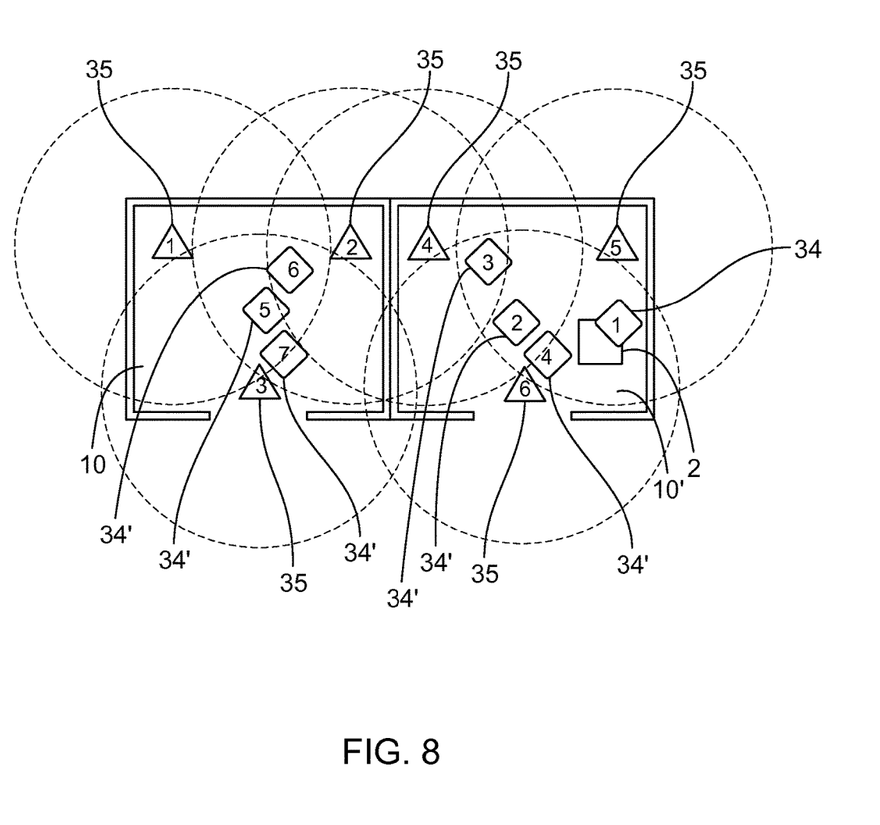
FIG. 8 shows a plan view of operating rooms with an arrangement of the medical apparatuses of FIG. 2 having tags and an arrangement of reading modules for an exact determination of the position of the medical apparatuses.
Figure 9:
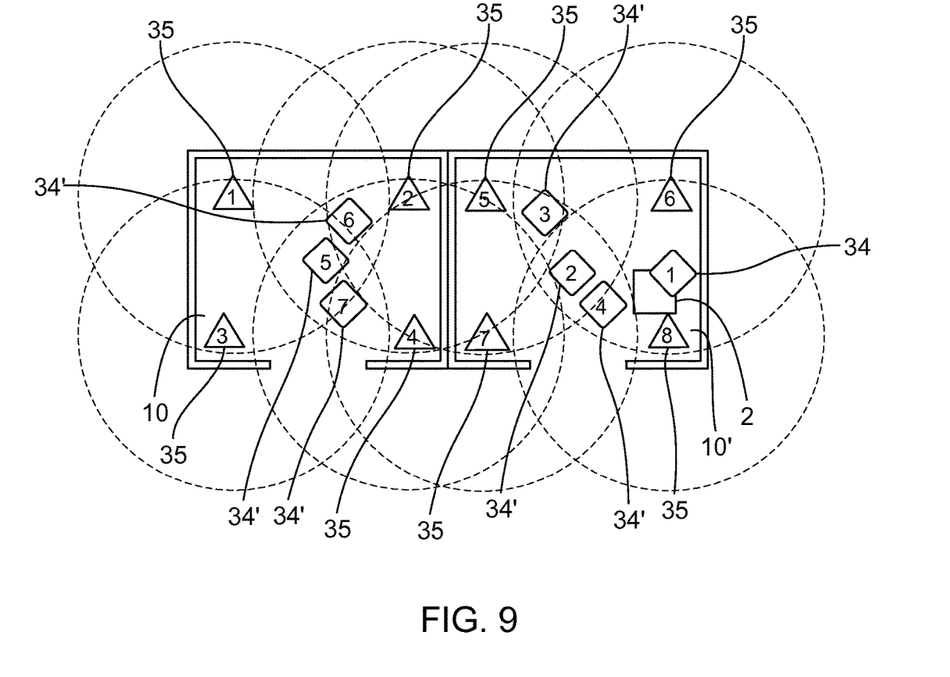
FIG. 9 shows a plan view of the operating rooms of FIG. 8 with an arrangement of the medical apparatuses of FIG. 2 having the tags and an arrangement of the reading modules for a simpler determination of the position.

A localization of the operator device 2 and of the medical apparatuses 5, 6, 7, 8 is shown in FIG. 8 and FIG. 9. FIGS. 8 and 9 respectively show a plan view of two operating rooms 10, 10' with an arrangement of the operator device 2, the medical apparatuses 5, 6, 7, 8, and an arrangement of reading modules 35 for an exact determination of positions of the medical apparatuses 5, 6, 7, 8 and of the operator device 2.

The operator device 2 is provided with a Bluetooth low energy transmitting module, a first transmitting unit or a so-called tag 34 and the medical apparatuses 5, 6, 7, 8 are provided with a second transmitting unit or so-called tag 34'. The tag 34 of the operator device 2 is included in a separate casing in which the operator device 2 is accommodated or, alternatively, included in the operator device 2, itself. All medical apparatuses 5, 6, 7, 8 to be illustrated on the operator device 2 (e.g., on a start screen) are provided with a tag 34'. The tags 34, 34' transmit identification information to identify the operator device 2 and the medical apparatuses 5, 6, 7, 8 as electromagnetic radiation (in this example, a radio signal) in periodic intervals (e.g., cyclically). A MAC address or a name is emitted. Alternatively, the information may be continuously transmitted or, for example, transmitted only upon a detected movement of the operator device 2 or detected movements of the medical apparatuses 5, 6, 7, 8.

In the operating rooms 10, 10', the reading modules 35 are provided. The reading modules 35 are provided at the ceiling of the operating room 10, 10' or, alternatively, at walls of the operating rooms 10, 10'. The reading modules 35 detect the strength of the electromagnetic radiation (e.g., a radio signal) of the respective tags 34, 34', act as a Bluetooth low energy reading module, and pass the electromagnetic radiation to the control device 4 via a data connection. Alternatively, infrared beams can be radiated by the transmitting units 34, 34' and can be received from the reading modules 35, or the transmitting units 34, 34' can be formed as ultra wide band transmitting modules and the reading modules 35 an be formed as ultra wide band reading modules. In a further alternative embodiment, a distribution of the medical apparatuses 5, 6, 7, 8 can be determined by optical tracking.

These reading modules 35 are respectively arranged at predefined positions in the operating rooms 10, 10'. The medical control system 1 is adapted such that, by the detected strength of the signals of the tags 34, 34', relative positions of the medical apparatuses 5, 6, 7, 8 having the tags 34' to the operator devices 2 having the tag 34 are determined and passed to the operator device 2.

The operator device 2 is adapted such that, controlled by the control device 4, it displays the schematic illustration of the medical apparatuses 5, 6, 7, 8 according to their relative positions to the operator device 2 so that the arrangement of the positions of the medical apparatuses 5, 6, 7, 8 illustrated on the operator device 2 correspond to the arrangement of the medical apparatuses 5, 6, 7, 8 from the view of the position of the operator device 2.

In FIG. 8, three reading modules 35 are respectively arranged in each operating room 10, 10'. The circles around the reading modules 35 illustrated by dashed lines show receiving rooms in which the reading modules 35 receive the signals of the tags 34, 34'. However, the dashed lines do not bound these receiving rooms.

Further, in FIG. 8, three tags 34' respectively attached to one of the medical apparatuses 5, 6, 7, 8 are respectively shown in each of the operating rooms 10, 10'. In one of the operating rooms 10, 10', the operator device 2 having the tag 34 is further shown. The positions of the tags 34' at the medical apparatuses 5, 6, 7, 8 and of the tags 34 at the operator device 2 and, therefore, the relative positions of the medical apparatuses 5, 6, 7, 8 to the operator device 2, are determined by the medical control system 1 by a triangulation. Accordingly, the relative positions of the medical apparatuses 5, 6, 7, 8 to the operator device 2 are determined by a detection of the signal strengths at the reading modules 35 and, subsequently, a position of the tags 34, 34' is determined.

In FIG. 9, a simpler determination of position is shown. In the plan view of the operating rooms 10, 10', the tag 34 at the operator device 2 and the tags 34' at the medical apparatuses 5, 6, 7, 8 are shown at positions similar to those shown in FIG. 8. However, in FIG. 9, four reading modules 35 are arranged in each of the operating rooms 10, 10'. The circles around the reading modules 35 illustrated by dashed lines also show receiving rooms in which the reading modules 35 receive the signals of the tags 34, 34'. However, the dashed lines do not bound these receiving rooms. As described below, the operating rooms 10, 10' include different areas which encompass the reading modules 35 and which are allocated to the reading modules 35. The position of the tags 34, 34' and, therefore, the relative position of the medical apparatuses 5, 6, 7, 8 to the operator device 2, are determined by a detection of the areas of the operating rooms 10, 10' in which the tags 34, 34' are located by the medical control system 1. The area allocated to the single reading module 35 which receives the highest value of the signal strength of the tag 34 of the operator device 2 is the area in which the user with the operator device 2 actually resides. Alternatively or additionally, the signal of further areas can also be evaluated if, for example, the tag 34, 34' is between two areas of the rooms or if several tags are in one area.

In an alternative embodiment, the operator device 2 is formed such that, upon operation, the operation functions of the medical apparatuses 5, 6, 7, 8 are already depicted on the first display of the start screen and can be activated thereon. Accordingly, the second display may be omitted, or the second display may omit the display of the symbols for the operation functions. Alternatively, the display having the arrangement of the medical apparatuses 5, 6, 7, 8 may not be the start screen but may be activated by a predetermined input.

Figure 10:
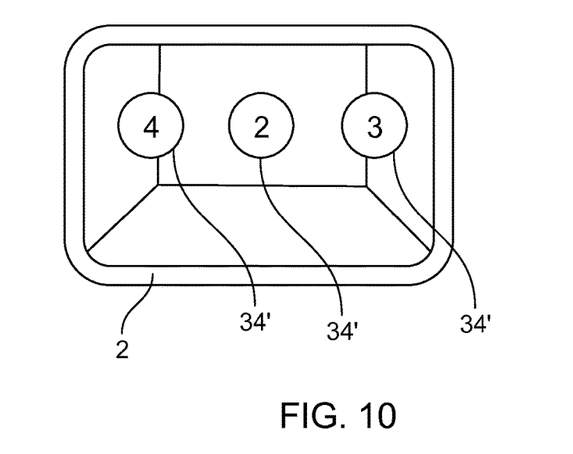
FIG. 10 shows a start screen of the touchscreen of FIG. 2 with a schematic arrangement of the medical apparatuses of FIG. 2 having the tags.

In use, the tag 34 of the operator device 2 and the tags 34' of the medical apparatuses 5, 6, 7, 8 respectively send information (e.g., their MAC addresses or their names) via electromagnetic rays. This information is received by the reading modules 35. The signal strength of the respective electromagnetic rays of the tags 34, 34' are measured at the reading modules 35, and the medical control system 1 determines the relative positions of the tags 34, 34' and, therefore, the relative positions of the medical apparatuses 5, 6, 7, 8, to the tag 34 at the operator device 2 by the signal strengths via a triangulation. Theses relative positions are transmitted to the operator device 2, and the operator device 2 shows the schematic illustration of the medical apparatuses 5, 6, 7, 8 according to the relative positions (see FIG. 10) on a start screen. Therefore, an arrangement of positions of the medical apparatuses 5, 6, 7, 8 depicted on the operator device 2 corresponds to an arrangement of the medical apparatuses 5, 6, 7, 8 from a view from a position of the operator device 2. Therefore, it is assumed that a user of the operator device 2 stands with his or her back to a wall of the room and views the center of the room and, therefore, the medical apparatuses 5, 6, 7, 8 therein.

By the triangulation of the signal strengths according to the configuration shown in FIG. 8, it is possible to determine the exact position of the tags 34, 34' and, therefore, their relative positions to each other. By the detected signal strength, the distance of a certain tag 34, 34' from the three reading modules 35 is determined. By the evaluation of the distances of the certain tag 34, 34' from the three reading modules 35, wherein a circle with the detected distance is respectively virtually placed around the reading modules 35 and wherein the position of the certain tag 34, 34' is placed in the intersection point of these circles, and by the knowledge of the position of the reading modules, the position of the certain tag 34, 34' is determined. The medical apparatus 5, 6, 7, 8 having the tag 34'-4 is therefore illustrated on a left region of the operator device 2, the medical apparatus 5, 6, 7, 8 having the tag 34'-2 is illustrated on a central region of the operator device 2, and the medical apparatus 5, 6, 7, 8 having the tag 34'-3 is illustrated on a right region of the operator device 2 (see FIG. 10).

By the configuration shown in FIG. 9, it is possible to ascertain in which area of the operating rooms 10, 10' one of the tags 34, 34' is located. The tags 34, 34' can be arranged in the upper left area (reading module 35-1, reading module 35-5), in the upper right area (reading module 35-2, reading module 35-6), in the lower left area (reading module 35-3, reading module 35-7), and in the lower right area (reading module 35-4, reading module 35-8). Here, the tag 34'-1 is located in the lower right area in the vicinity of the reading module 35-8, tag 34'-2 is located in the lower left area in the vicinity of reading module 35-7, and tag 34'-4 is located in the lower right area in the vicinity of the reading module 35-8. By an evaluation, it is determined that the user with the operator device 2 (tag 34-1) is situated in the corner in the lower right area of the operating room 10' and that he looks towards the center of the room or in a direction of the medical apparatuses 5, 6, 7, 8. On the start screen (FIG. 10), the medical apparatus having the tag 34'-4 is depicted on the left portion of the operator device 2, the medical apparatus having the tag 34'-2 is depicted in the center portion of the operator device 2, and the medical apparatus having the tag 34'-3 is depicted on the right portion of the operator device 2.

A further alternative method includes a determination and storing of signal strengths for predefined positions of the tags 34, 34' or of their coordinates in the operating room 10, 10'. The signal strengths are received at at least three reading modules 35. The predefined position with associated coordinates is stored together with the respective allocated signal strengths in the medical control system 1 in a database. A suitable number of predefined positions is stored with the signal strengths in order to ensure a required accuracy of the system. In use, the respective signal strengths at the reading modules 35 are detected, and the resulting coordinates in the database are allocated for the respective positions of the tags 34, 34'.

A number of embodiments have been described. Nevertheless, it will be understood that various modifications may be made without departing from the spirit and scope of the disclosure. Accordingly, other embodiments are within the scope of the following claims. For example, the different embodiments and alternatives of the medical control system 1 are combinable.

What is claimed is:
1. A medical control system, comprising:
an operator device having a touchscreen;
a control device; and
a plurality of medical apparatuses, wherein the plurality of medical apparatuses and the operator device are coupled to the control device by respective data connections, wherein the operator device is adapted to display a plurality of schematic illustrations respectively corresponding to each of the plurality of medical apparatuses in a first display on the touchscreen, wherein the operator device is adapted, by touching a first schematic illustration of the plurality of schematic illustrations in the first display, to illustrate a first medical apparatus of the plurality of medical apparatuses along with first specific operation functions of the first medical apparatus in a second display, wherein the first and second displays comprise substantially similar symbols for respectively illustrating substantially similar specific operation functions of the plurality of medical apparatuses, and wherein the first medical apparatus illustrated in the second display comprises driven components, and the operator device is adapted to illustrate the driven components by symbols that correspond to specific operation functions.

2. The medical control system according to claim 1, wherein the operator device is adapted, by touching an illustration of a first component of the driven components, to illustrate a direction of movement of the first driven component and default speeds for movement of the first driven component in a third display.

3. The medical control system according to claim 2, wherein the operator device comprises a display for displaying information associated with an actual position of the first driven component in the direction of movement.

4. The medical control system according to claim 1, wherein the specific operation functions comprise moving of one or more of the driven components into a respective predefined position, and the operator device is adapted, by touching a preset symbol for moving the one or more of the driven components into the respective predefined position in the second display, to illustrate end positions of the driven components and default speeds for movement of the driven components in a third display.

5. The medical control system according to claim 4, wherein a plurality of preset symbols are provided to respectively control different predefined positions.

6. The medical control system according to claim 4, wherein the medical control system is adapted, by touching a saving symbol, to store respective actual positions of the driven components.

7. The medical control system according to claim 1, wherein the operator device is adapted, by touching a second schematic illustration of the plurality of schematic illustrations in the first display, to illustrate a second medical apparatus of the plurality of medical apparatuses along with second specific operation functions of the second medical apparatus in a second display, wherein the second medical apparatus illustrated in the second display comprises lighting components, and the operator device is adapted to enable the lighting components by illustrating first operational symbols for controlling the second specific operation functions in the second display.

8. The medical control system according to claim 7, wherein the operator device is adapted to illustrate second operational symbols corresponding to adjustable parameters by touching a particular symbol of the first operational symbols for controlling the specific operation functions.

9. The medical control system according to claim 8, wherein the second specific operation functions comprise a brightness setting.

10. The medical control system according to claim 8, wherein the second specific operation functions comprise an adjustment of a size of a light field.

11. The medical control system according to claim 8, wherein the second specific operation functions comprise an adjustment of a color temperature.

12. The medical control system according to claim 8, wherein the second specific operation functions comprise a selection of operated lighting components.

13. The medical control system according to claim 1, wherein the operator device provides a three-dimensional illustration of the room and the plurality of medical apparatuses.

14. The medical control system according to claim 13, wherein the operator device is adapted to modify the three-dimensional illustration depending on a position of the operator device such that the three-dimensional illustration corresponds to a view of the room from a perspective of the operator device.

15. The medical control system according to claim 1, wherein all of the plurality of medical apparatuses located in a specific room are displayed.

16. The medical control system according to claim 1, wherein any of the plurality of medical apparatuses that are not operated are displayed in a different manner in the first and second displays than are the medical apparatuses that are operated.

17. The medical control system according to claim 1, wherein an illustrated configuration of the plurality of medical apparatuses corresponds to a predetermined configuration of the medical control device.

18. The medical control system according to claim 17, wherein an illustrated configuration of the plurality of medical apparatuses corresponds to a configuration associated with a user of the medical control system.

19. The medical control system according to claim 17, wherein an illustrated configuration of the plurality of medical apparatuses corresponds to a configuration associated with a particular application of the plurality of medical apparatuses.

20. A medical control system, comprising:
an operator device having a touchscreen, the operator device comprising a first transmitting unit that emits electromagnetic radiation;
a control device;
a plurality of medical apparatuses comprising second transmitting units that emit electromagnetic radiation,
wherein the plurality of medical apparatuses and the operator device are coupled to the control device with respective data connections,
wherein the operator device is adapted to display a plurality of schematic illustrations respectively corresponding to the plurality of medical apparatuses on the touchscreen,
wherein the operator device is adapted, by touching a first schematic illustration of the plurality of schematic illustrations, to illustrate specific operation functions of a first medical apparatus of the plurality of medical apparatuses,
the medical control device further comprising a plurality of reading modules for receiving the electromagnetic radiation emitted by the first and second transmitting units arranged at predefined positions, wherein the medical control system is adapted, by a measurement of signal strengths of the electromagnetic radiation received by the plurality of reading modules, to determine and to transmit to the operator device relative positions of the plurality of medical apparatuses, and wherein the operator device is adapted to display the plurality of schematic illustrations of the plurality of medical apparatuses according to the relative positions so that an arrangement of the relative positions of the plurality of medical apparatuses illustrated on the operator device corresponds to an arrangement of the plurality of medical apparatuses as viewed from a perspective of the operator device.

21. The medical control system according to claim 20, wherein the first and second transmitting units are provided as radio transmitting units, and the plurality of reading modules are provided as radio receiving units.

22. The medical control system according to claim 21, wherein the first and second transmitting units are provided as low energy Bluetooth transmitting units, and the plurality of reading modules are provided as low energy Bluetooth reading modules.

23. The medical control system according to claim 21, wherein the first and second transmitting units are provided as ultra wideband transmitting modules, and the plurality of reading modules are provided as ultra wideband reading modules.

24. The medical control system according to claim 20, wherein the plurality of reading modules are arranged at a ceiling of a room.

25. The medical control system according to claim 20, wherein the first and second transmitting units are configured to cyclically emit identification information.

26. The medical control system according to claim 20, wherein three reading modules are arranged in a room, and the medical control system is adapted to determine the relative positions of the operator device and of the plurality of medical apparatuses via a triangulation of the signal strengths.

27. The medical control system according to claim 20, wherein at least four reading modules are arranged in a room, and the medical control system is adapted to determine the relative positions of the operator device to the plurality of medical apparatuses via an area determination.

28. The medical control system according to claim 20, wherein at least three reading modules are arranged in a room, and the medical control system is adapted to store and recall coordinates of predefined positions of the operator device and of the plurality of medical apparatuses in the room and respective related signal strengths received by the at least three reading modules in order to determine the relative positions of the operator device to the plurality of medical apparatuses via the coordinates based on the respective related signal strengths.

* * * * *